(12) United States Patent
Wolleschensky et al.

(10) Patent No.: US 6,858,852 B2
(45) Date of Patent: Feb. 22, 2005

(54) METHOD AND APPARATUS FOR RAPID CHANGE OF FLUORESCENCE BANDS IN THE DETECTION OF DYES IN FLUORESCENCE MICROSCOPY

(75) Inventors: Ralf Wolleschensky, Schoeten (DE); Gunter Moehler, Jena (DE)

(73) Assignee: Carl Zeiss Jena GmbH, Jena (DE)

( * ) Notice: Subject to any disclaimer, the term of this patent is extended or adjusted under 35 U.S.C. 154(b) by 263 days.

(21) Appl. No.: 09/924,315

(22) Filed: Aug. 7, 2001

(65) Prior Publication Data

US 2002/0020819 A1 Feb. 21, 2002

Related U.S. Application Data

(60) Provisional application No. 60/230,342, filed on Sep. 6, 2000.

(30) Foreign Application Priority Data

Aug. 8, 2000 (DE) ......................................... 100 38 526

(51) Int. Cl.$^7$ .......................... G01N 21/64; G01N 21/17
(52) U.S. Cl. .............................. 250/459.1; 250/339.01; 250/339.02; 356/317; 356/319; 356/326
(58) Field of Search .......................... 250/459.1, 458.1, 250/461.1, 461.2, 339.01, 339.02, 339.07; 356/317, 318, 319, 320, 326, 417

(56) References Cited

U.S. PATENT DOCUMENTS

| | | | |
|---|---|---|---|
| 4,669,880 A | 6/1987 | Nelson et al. | |
| 4,844,617 A | 7/1989 | Kelderman et al. | |
| 5,108,179 A | * 4/1992 | Myers | 356/344 |
| 5,192,980 A | 3/1993 | Dixon et al. | |
| 5,329,352 A | 7/1994 | Jacobsen | |
| 5,461,477 A | 10/1995 | Marinelli et al. | |
| 5,479,255 A | * 12/1995 | Denny et al. | 356/319 |
| 5,528,368 A | 6/1996 | Lewis et al. | |
| 5,539,517 A | 7/1996 | Cabib et al. | |
| 5,638,173 A | 6/1997 | Smith et al. | |
| 5,689,333 A | 11/1997 | Batchelder et al. | |

(List continued on next page.)

FOREIGN PATENT DOCUMENTS

| | | |
|---|---|---|
| DE | 34 32 252 A1 | 3/1986 |
| DE | 694 02 958 | 2/1993 |
| DE | 693 27 909 | 7/1993 |
| DE | 197 02 914 | 1/1997 |
| DE | 198 01 139 | 7/1999 |
| DE | 198 29 944 | 1/2000 |
| DE | 199 15 137 A1 | 10/2000 |
| DE | 296 24 210 U1 | 6/2001 |
| DE | 100 38 049 A1 | 2/2002 |
| EP | 0 548 830 A1 | 12/1992 |
| EP | 0 647 838 | 4/1995 |
| WO | WO 00/31577 | 6/2000 |
| WO | WO 01/09592 A1 | 2/2001 |

OTHER PUBLICATIONS

English Abstract of DE 34 32 252 A1.
English Abstract of DE 296 24 210 U1.

(List continued on next page.)

Primary Examiner—Albert Gagliardi
(74) Attorney, Agent, or Firm—Reed Smith LLP (57) ABSTRACT

A method is disclosed for operation of an image-generating optical system for detection of characteristic quantities of the wavelength-dependent behavior of an illuminated specimen, such as the emission behavior and/or absorption behavior and, in particular, the fluorescence and/or luminescence and/or phosphorescence and/or enzyme-active light emission and/or enzyme-active fluorescence, for the operation of a laser scanning microscope, comprising the steps of splitting the image point information of the specimen into spectral components in a spatially resolved manner on the detection side in dependence on wavelength and carrying out at least one summing for different spectral components.

86 Claims, 9 Drawing Sheets

U.S. PATENT DOCUMENTS

| | | | |
|---|---|---|---|
| 5,731,874 A | * 3/1998 | Maluf | 356/326 |
| 5,760,899 A | 6/1998 | Eismann | |
| 5,784,162 A | 7/1998 | Cabib et al. | |
| 5,817,462 A | 10/1998 | Garini et al. | |
| 5,886,784 A | 3/1999 | Engelhardt | |
| 6,038,023 A | * 3/2000 | Carlson et al. | 356/326 |
| 6,040,907 A | 3/2000 | Steiner et al. | |
| 6,252,236 B1 | * 6/2001 | Trulson et al. | 250/458.1 |
| 6,271,917 B1 | * 8/2001 | Hagler | 356/310 |
| 6,317,207 B2 | * 11/2001 | French et al. | 356/317 |
| 6,337,472 B1 | 1/2002 | Garner et al. | |
| 6,403,947 B1 | * 6/2002 | Hoyt et al. | 250/226 |

OTHER PUBLICATIONS

English Abstract of DE 199 15 137 A1.

English Abstract of DE 100 38 049 A1.

Article: "Resolution of multiple green fluorescent protein color variants and dyes using two–photon microscopy and imaging spectroscopy" Journal of Biomedical Optics Jul. 2001 vol. 6. No. 3 pp. 311–318.

*English Abstract of DE 198 01 139.

*English Abstract of DE 198 29 944.

* cited by examiner

METHOD AND APPARATUS FOR RAPID CHANGE OF FLUORESCENCE BANDS IN THE DETECTION OF DYES IN FLUORESCENCE MICROSCOPY

CROSS-REFERENCE TO RELATED APPLICATIONS

This application claims priority of provisional application Ser. No. 60/230,342, filed Sep. 6, 2000 and German Application No. 100 38 526.5, filed Aug. 8, 2000, the complete disclosures of which are hereby incorporated by reference.

BACKGROUND OF THE INVENTION a) Field of the Invention

The invention is directed to a method and an arrangement in fluorescence microscopy, particularly laser scanning microscopy, fluorescence correlation spectroscopy, and nearfield scanning microscopy, for examination of predominantly biological specimens, preparations and associated components. This includes methods for screening active ingredients based on fluorescence detection (high throughput screening). The transition from the detection of a few broad-spectrum dye bands to the simultaneous acquisition of whole spectra opens up new possibilities for the identification, separation and allocation of mostly analytic or functional specimen characteristics to spatial partial structures or dynamic processes. Therefore, simultaneous examination of specimens with multiple fluorophores with overlapping fluorescence spectra are even possible in spatial structures of thick specimens. The data acquisition rate is not reduced by the arrangement.

b) Description of the Related Art

A typical area of application of light microscopy for examining biological preparations is fluorescence microscopy (Pawley, "Handbook of Biological Confocal Microscopy"; Plenum Press 1995). In this case, determined dyes are used for specific labeling of cell parts.

Figure 1A:
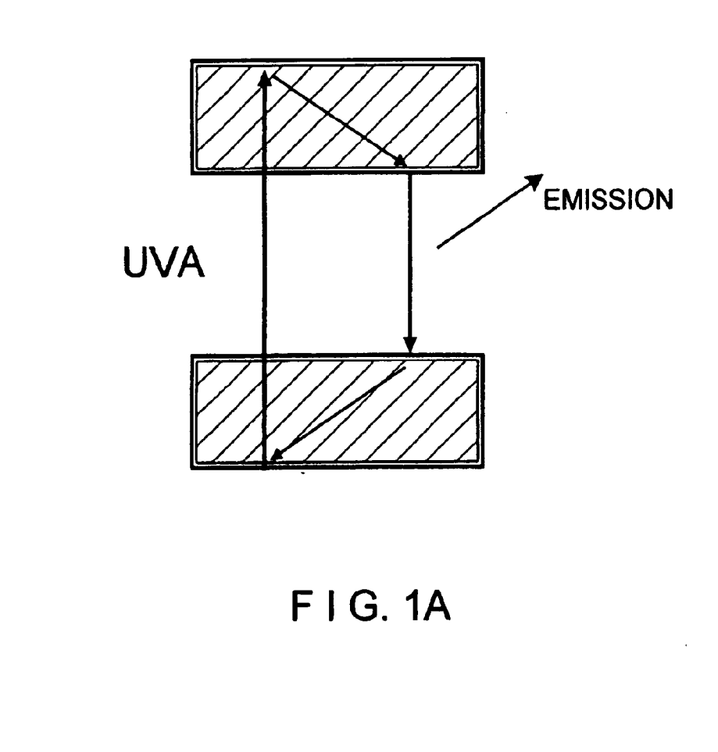
FIG. 1a illustrates one-photon absorption.

The irradiated photons having a determined energy excite the dye molecules, through the absorption of a photon, from the ground state to an excited state. This excitation is usually referred to as one-photon or single-photon absorption (FIG. 1a). The dye molecules excited in this way can return to the ground state in various ways. In fluorescence microscopy, the most important is the transition with emission of a fluorescence photon. Because of the Stokes shift, there is generally a red shift in the wavelength of the emitted photon in comparison to the excitation radiation; that is, it has a greater wavelength. Stokes shift makes it possible to separate the fluorescence radiation from the excitation radiation.

The fluorescent light is split off from the excitation radiation by suitable dichroic beam splitters in combination with blocking filters and is observed separately. This makes it possible to show individual cell parts that are dyed with different dyes. In principle, however, several parts of a preparation can also be dyed simultaneously with different dyes which bind in a specific manner (multiple fluorescence). Special dichroic beam splitters are used again to distinguish the fluorescence signals emitted by the individual dyes.

Figure 1B:
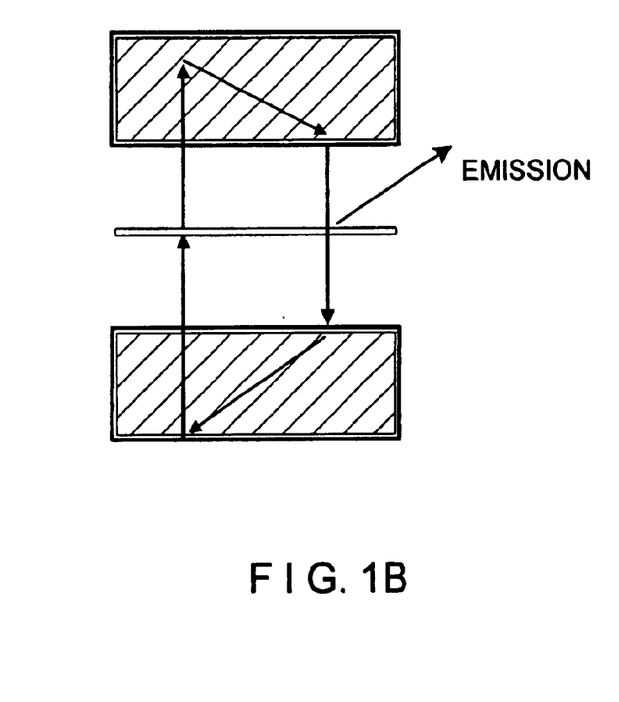
FIG. 1b illustrates multiphoton absorption.

In addition to excitation of dye molecules with a high-energy photon (single-photon absorption), excitation with a plurality of low-energy photons is also possible (FIG. 1b). The sum of energies of the single photons corresponds approximately to a multiple of the high-energy photon. This type of excitation of dyes is known as multiphoton absorption (Corle, Kino, "Confocal Scanning, Optical Microscopy and Related Imaging Systems"; Academic Press 1996). However, the dye emission is not influenced by this type of excitation, i.e., the emission spectrum undergoes a negative Stokes shift in multiphoton absorption; that is, it has a smaller wavelength compared to the excitation radiation. The separation of the excitation radiation from the emission radiation is carried out in the same way as in single-photon excitation.

Figure 2:
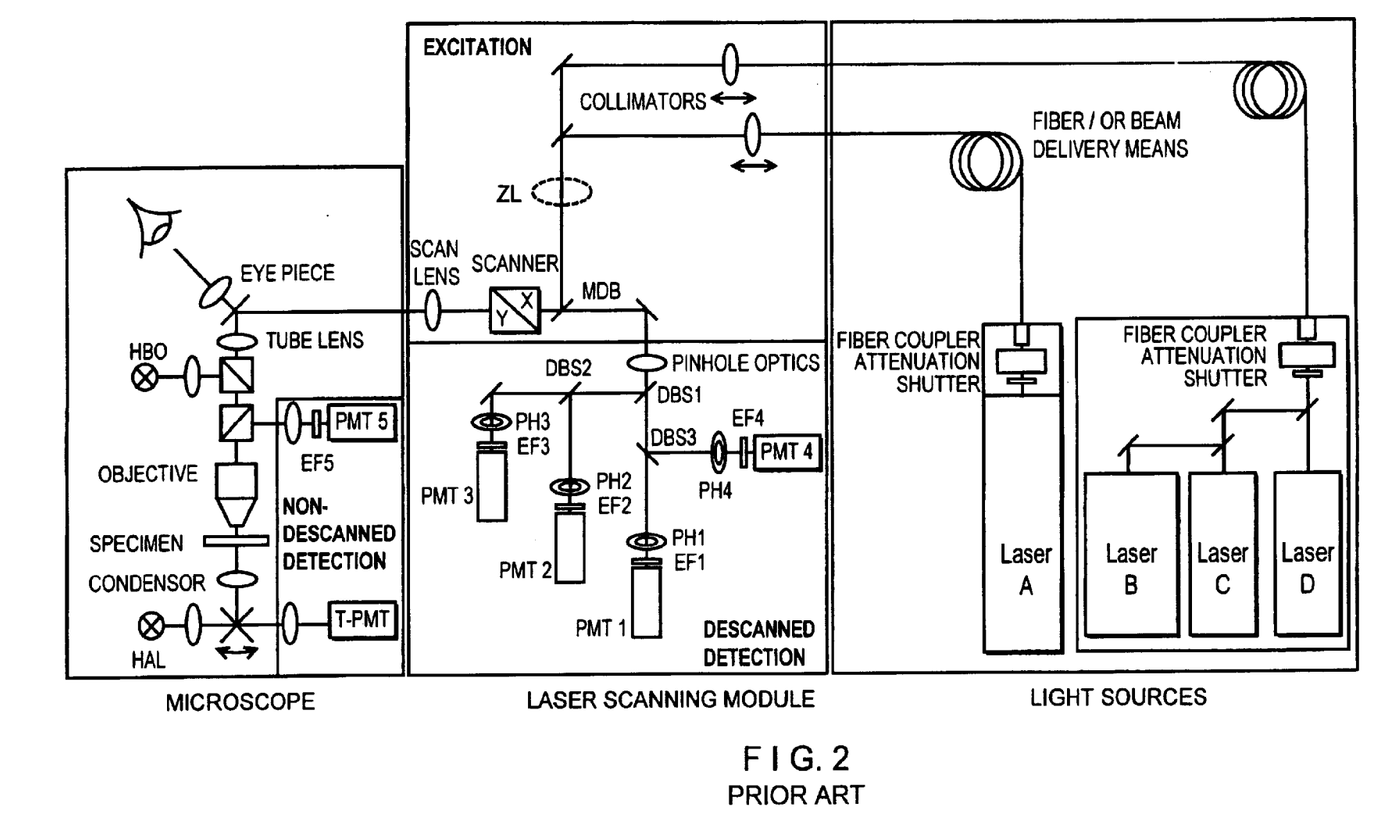
FIG. 2 illustrates an LSM construction in accordance with the prior art.

The prior art will be explained more fully in the following by way of example with reference to a confocal laser scanning microscope (LSM) (FIG. 2[L1].

An LSM is essentially composed of four modules: light source, scan module, detection unit and microscope. These modules are described more fully in the following. In addition, reference is had to DE19702753A1.

Lasers with different wavelengths are used in an LSM for specific excitation of different dyes in a preparation. The choice of excitation wavelengths is governed by the absorption characteristics of the dyes to be examined. The excitation radiation is generated in the light source module. Various lasers (argon, argon/krypton, Ti:Sa lasers) are used for this purpose. Further, the selection of wavelengths and the adjustment of the intensity of the required excitation wavelength is carried out in the light source module, e.g., using an acousto-optic crystal. The laser radiation subsequently reaches the scan module via a fiber or a suitable mirror arrangement.

The laser radiation generated in the light source is focussed in the preparation in a diffraction-limited manner by means of the objective via the scanner, scanning optics and tube lens. The focus scans the specimen in a point raster in x-y direction. The pixel dwell times when scanning over the specimen are mostly in the range of less than one microsecond to several seconds.

In confocal detection (descanned detection) of fluorescent light, the light emitted from the focal plane (specimen) and from the planes located above and below the latter reaches a dichroic beam splitter (MDB) via the scanner. This dichroic beam splitter separates the fluorescent light from the excitation light. The fluorescent light is subsequently focused on a diaphragm (confocal diaphragm/pinhole) located precisely in a plane conjugate to the focal plane. In this way, fluorescent light components outside of the focus are suppressed. The optical resolution of the microscope can be adjusted by varying the size of the diaphragm. Another dichroic blocking filter (EF) which again suppresses the excitation radiation is located behind the diaphragm. After passing the blocking filter, the fluorescent light is measured by means of a point detector (PMT).

When using multiphoton absorption, the excitation of the dye fluorescence is carried out in a small volume at which the excitation intensity is particularly high. This area is only negligibly larger than the detected area when using a confocal arrangement. Accordingly, a confocal diaphragm can be dispensed with and detection can be carried out directly following the objective (non-descanned detection).

In another arrangement for detecting a dye fluorescence excited by multiphoton absorption, descanned detection is carried out again, but this time the pupil of the objective is imaged in the detection unit (nonconfocal descanned detection).

From a three-dimensionally illuminated image, only the plane (optical section or slice) located in the focal plane of the objective is reproduced by the two detection arrangements in connection with corresponding single-photon absorption or multiphoton absorption. By recording or plotting a plurality of optical slices in the x-y plane at different depths z of the specimen, a three-dimensional image of the specimen can be generated subsequently in computer-assisted manner.

Accordingly, the LSM is suitable for examination of thick preparations. The excitation wavelengths are determined by the utilized dye with its specific absorption characteristics. Dichroic filters adapted to the emission characteristics of the dye ensure that only the fluorescent light emitted by the respective dye will be measured by the point detector.

Figure 3A:
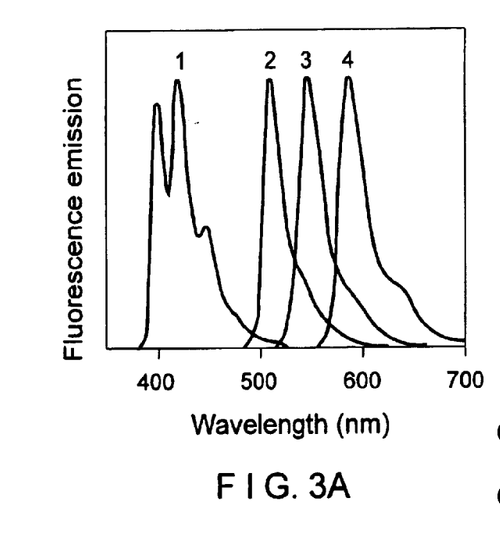
FIGS. 3a and 3b illustrates spectra for dyes and fluorescent proteins.

Currently, in biomedical applications, a number of different cell regions are labeled simultaneously by different dyes (multifluorescence). In the prior art, the individual dyes can be detected separately based on different absorption characteristics or emission characteristics (spectra) (FIG. 3a). FIG. 3a shows the emission spectra of various typical dyes. The emission signal is shown as a function of wavelength. It will be noted that the dyes designated by 1 to 4 differ from one another with respect to the position and shape of their emission spectra. For separate detection, an additional splitting of the fluorescent light of a plurality of dyes is carried out with the secondary beam splitters (DBS) and a separate detection of the individual dye emissions is carried out in different point detectors (PMT x). With the arrangement described above, it is impossible for the user to flexibly adapt detection and excitation to corresponding new dye characteristics. Instead, new dichroic beam splitters and blocking filters must be created for every (new) dye.

In an arrangement according to WO95/07447, the fluorescent light is split spectrally by means of a prism. The method differs from the above-described arrangement with dichroic filters only in that the characteristic of the utilized filter is adjustable. However, it is still preferable to record the emission band of a dye by point detector.

Figure 3B:
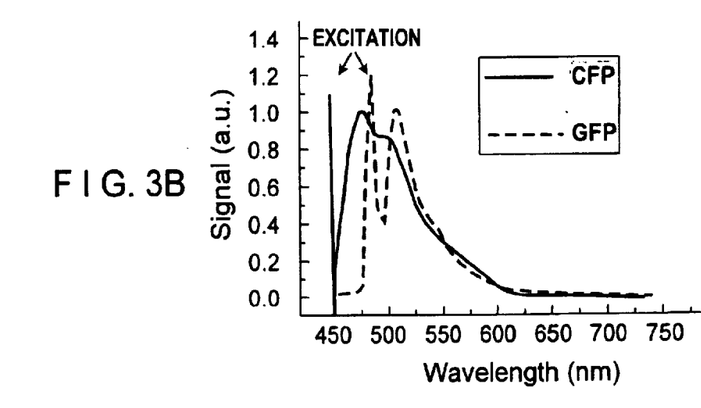

A fast change in detection regions is possible only conditionally with the two arrangements, since the adjustment of the emission range relies on mechanical movements of the dichroic filter and diaphragms. A fast change is needed, for example, when the emission spectra overlap, as is shown in FIG. 3b, but the absorption characteristics are different. FIG. 3b shows the emission signals as a function of the wavelength for the dyes CFP, Topas, CFT and Cyan-FP. This method (multitracking) is described in DE 19829981A1. These dyes are particularly suited to examination of living preparations because they have no toxic effects on the specimens to be examined. In order to be able to detect both dyes, CFP and CFT, as efficiently as possible, excitation is carried out in one scanning direction CFP with a wavelength of 458 nm and the fluorescence of 460–550 nm is detected. On the return path of the scanner, selective excitation of GFP is carried out at 488 nm and the wavelength range of 490–650 nm is detected.

Figure 3C:
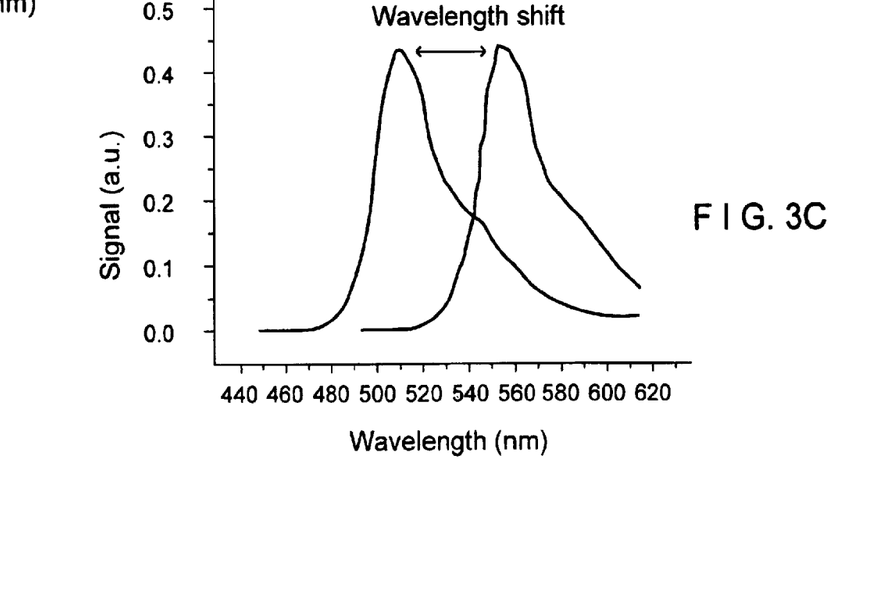
FIG. 3c illustrates wavelength shift as a function of environment.

When the position of the emission spectrum of the utilized dyes is unknown or when a shift occurs in the emission spectrum depending on environment (FIG. 3c), efficient detection of the dye fluorescence is possible only conditionally. The emission signal is shown again in FIG. 3c as a function of the wavelength. The wavelength shift can amount to several times 10 nm. Spectrometers are also currently used in combination with an LSM to measure the emission spectrum in the specimen. In so doing, a conventional, usually high-resolution spectrometer is used instead of a point detector (Patent: Dixon, et al. U.S. Pat. No. 5,192,980). However, these spectrometers can record an emission spectrum only point by point or as an average over a region. Thus, this is a type of spectroscopy.

Figure 4A:
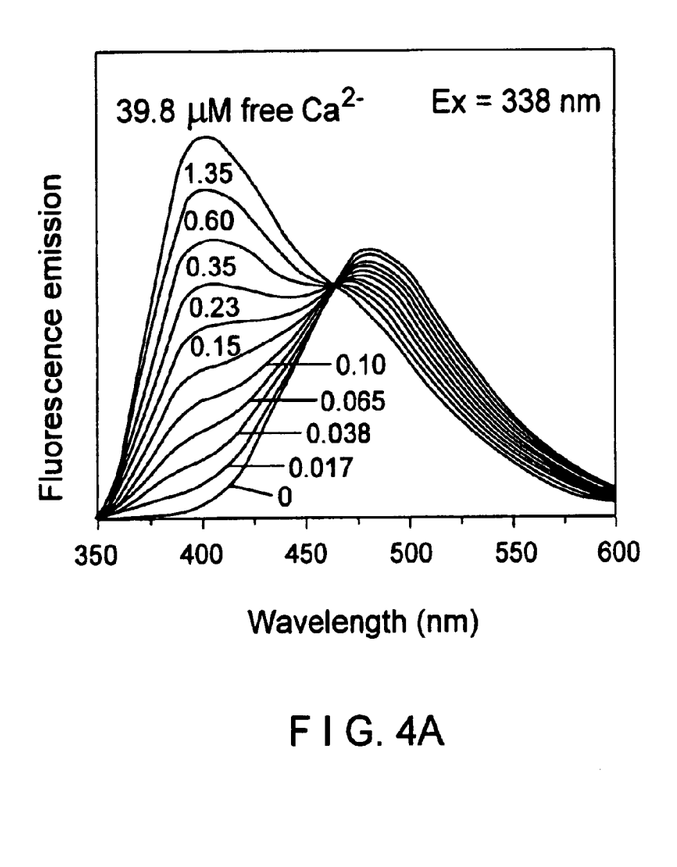
FIGS. 4a and 4b illustrate typical spectra with ratiometric measurements.
Figure 4B:
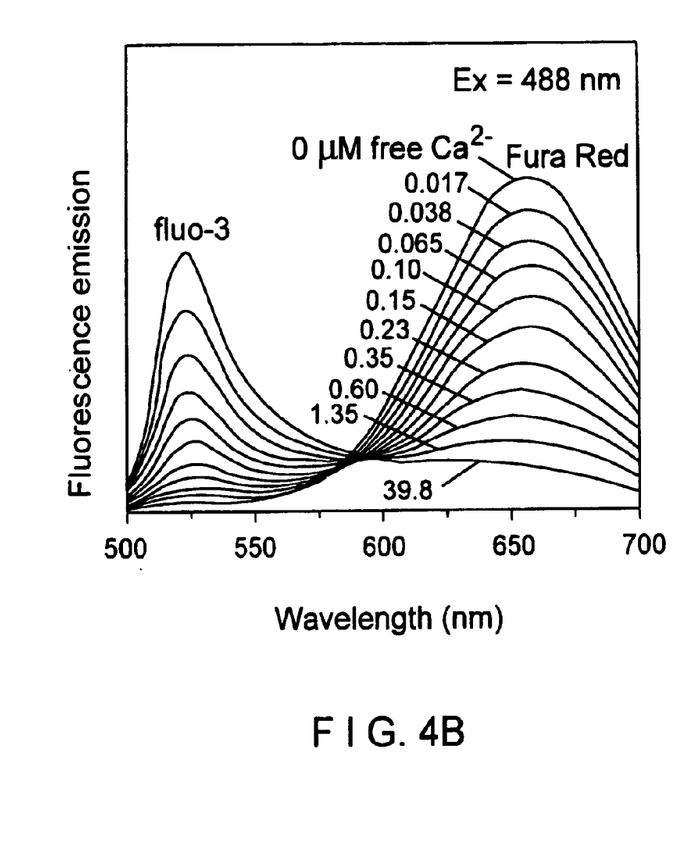

In another application of fluorescence microscopy, the ion concentration (e.g., $Ca^+$, $K^+$, $Mg^{2+}$, $ZN^+$, ...) is determined, particularly in biological preparations. Special dyes or dye combinations (e.g., Fura, Indo, Fluo; Molecular Probes, Inc.) having a spectral shift depending on the ion concentration are used for this purpose. FIG. 4a shows the emission spectra of Indo-1 as a function of the concentration of calcium ions. FIG. 4b shows an example of the emission spectra depending on the calcium ion concentration using the combination of Fluo-3 and Fura Red dyes. These special dyes are known as emission ratio dyes. When the two fluorescence regions shown in FIG. 4a are summed and the ratio of both intensities is taken, the corresponding ion concentration can be determined. In these measurements, the examination is usually directed to dynamic change in the ion concentration in living preparations requiring a time resolution of less than one millisecond.

OBJECT AND SUMMARY OF THE INVENTION

Therefore, the primary object of the invention is the provision of novel methods for flexible and freely programmable detection. These methods should be usable in image-generating and analytic microscopy systems. The microscope systems are image-generating systems such as laser scanning microscopes for three-dimensional examination of biological preparations with an optical resolution of up to 200 nm, nearfield scanning microscopes for high-resolution examination of surfaces with a resolution of up to 10 nm, fluorescence correlation microscopes for quantitative determination of molecular concentrations and for measuring molecular diffusions. Also included are methods based on fluorescence detection for screening dyes.

In all of the systems mentioned above, fluorescence dyes are used for specific labeling of the preparation. This object is met in accordance with the invention by a method for operation of an image-generating optical system for detection of characteristic quantities of the wavelength-dependent behavior of an illuminated specimen, such as the emission behavior and/or absorption behavior and, in particular, the fluorescence and/or luminescence and/or phosphorescence and/or enzyme-active light emission and/or enzyme-active fluorescence, for the operation of a laser scanning microscope, comprising the steps of splitting the image point information of the specimen into spectral components in a spatially resolved manner on the detection side in dependence on wavelength and carrying out at least one summing for different spectral components.

Further in accordance with the invention, an arrangement for optical detection of characteristic quantities of the wavelength-dependent behavior of an illuminated specimen, such as the emission behavior and/or absorption behavior, in particular, the fluorescence and/or luminescence and/or phosphorescence and/or enzyme-active light emission and/or enzyme-active fluorescence, comprising a dispersive element for splitting the emission radiation spectrally, a detector for detecting radiation signal and means for electronically determining at least one sensor signal of the emission radiation and/or of the absorbed radiation.

DESCRIPTION OF THE PREFERRED EMBODIMENTS

Figure 5:
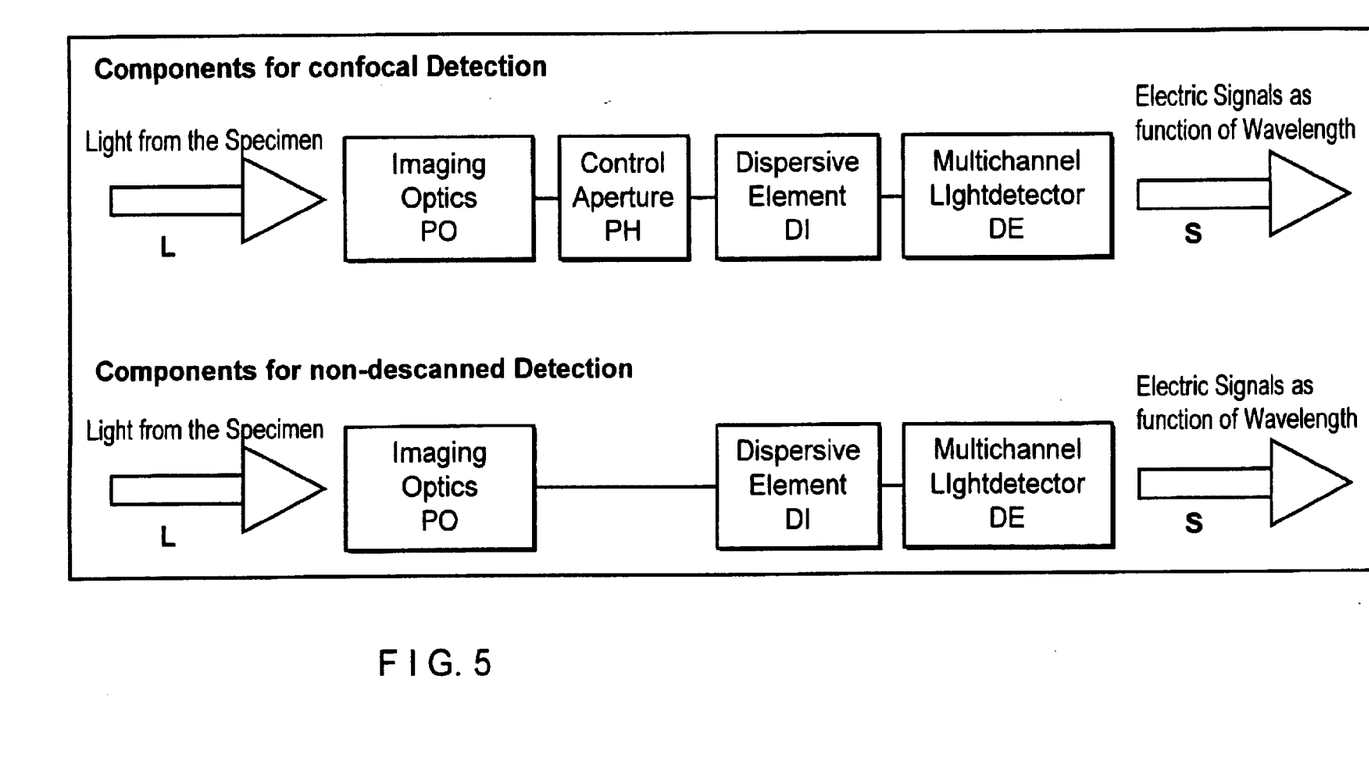
FIG. 5 is a block diagram of detector-optics construction.

The method according to the invention is based on a spectrally split detection of fluorescence. For this purpose, the emission light is split from the excitation light in the scan module or in the microscope (with multiphoton absorption) by means of an element for separating the excitation radiation from the detected radiation, such as the main color splitter (MDB) or an AOTF according to 7346DE or 7323DE. With transmitted-light arrangements, this type of element can also be entirely omitted. A block diagram of the detector unit to be described is shown in FIG. 5. With confocal detection, the light L from the specimen is focused through a diaphragm (pinhole) PH by means of imaging optics PO, so that fluorescence occurring outside of the focus is suppressed. In non-descanned detection, the diaphragm is omitted. The light is now divided into its spectral components by means of an angle-dispersive element DI. The angle-dispersive elements can be prisms, gratings and, e.g., acousto-optic elements. The light which is split into its spectral components by the dispersive element is subsequently imaged on a line detector DE. This line detector DE measures the emission signal S as a function of wavelength and converts it into electrical signals. In addition, a line filter for suppressing the excitation wavelengths can be arranged in front of the detection unit.

Figure 6:
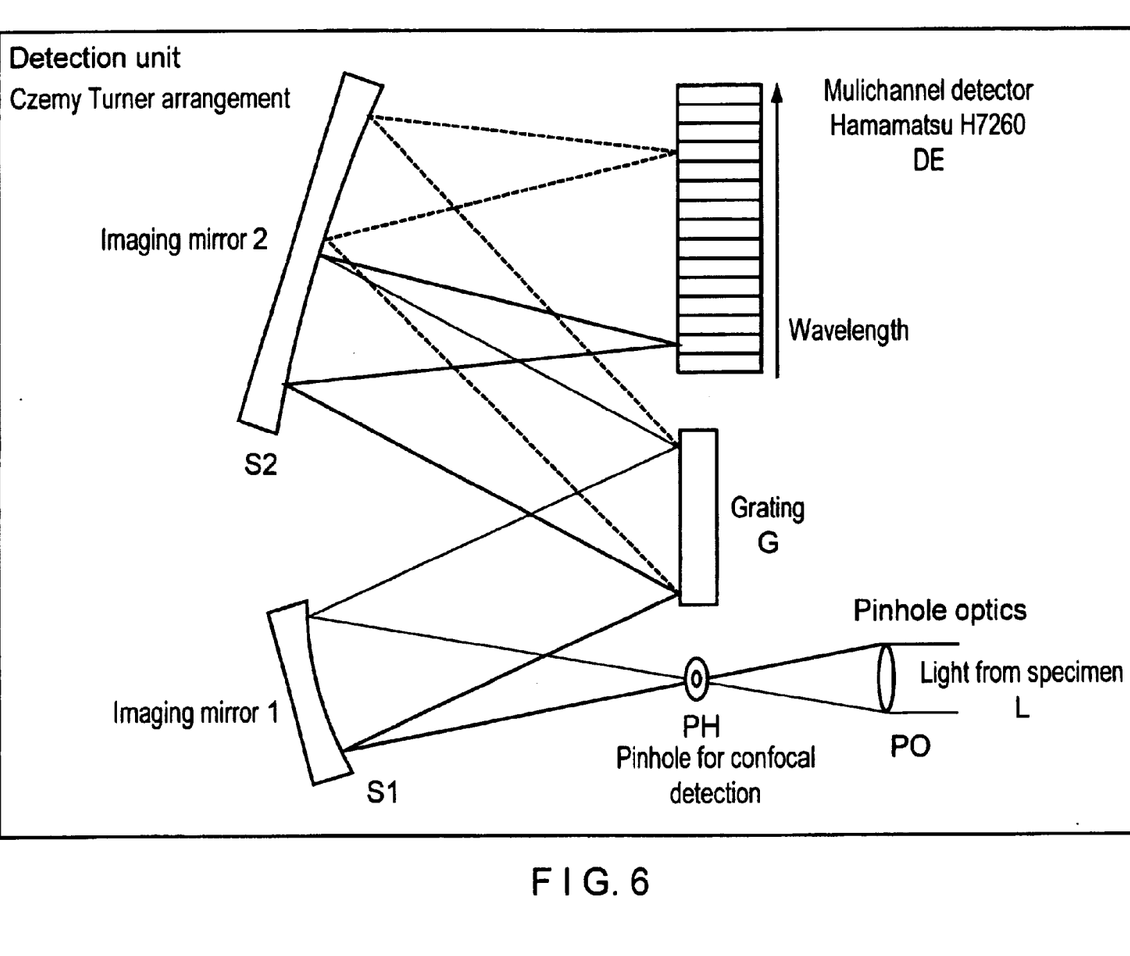
FIG. 6 is an example of detector unit/optics construction.

A possible embodiment form of the optical beam path of the detector unit shown in the block diagram in FIG. 5 is shown in FIG. 6. The construction is essentially a Czerny Turner construction. In confocal detection, the light L from the specimen is focused through the confocal diaphragm PH by the pinhole optics PO. With non-descanned detection in case of multiphoton absorption, this diaphragm can be omitted. The first imaging mirror S1 collimates the fluorescent light. Subsequently, the light strikes a line grating G, for example, a grating with a line number of 651 lines per mm. The grating bends the light in different directions corresponding to its wavelength. The second imaging mirror S2 focuses the individual spectrally split wavelength components on the corresponding channels of the line detector DE. The use of a secondary electron multiplier array by Hamamatsu H7260 is especially advantageous. The detector has 32 channels and high sensitivity. The free spectral region of the embodiment form described above is approximately 350 nm. In this arrangement, the free spectral region is uniformly distributed to the 32 channels of the line detector resulting in an optical resolution of approximately 10 nm. Therefore, this arrangement is suitable for spectroscopy only conditionally. However, its use in an image-generating system is advantageous because the signal per detection channel is still relatively large due to the relatively broad detected spectral band. A shift of the free spectral region can be carried out, in addition, by rotating the grating, for instance.

Another possible embodiment form could consist in the use of a matrix detector (e.g., a CCD manufactured by Sony, Kodak, etc.). In this case, splitting into different wavelength components is carried out in a coordinate through the dispersive element. A complete line (or column) of the scanned image is imaged in the other direction on the matrix detector. This embodiment form is particularly advantageous in the construction of a line scanner (Corle, Kino, "Confocal Scanning Optical Microscopy and Related Imaging Systems"; Academic Press 1996). The basic construction essentially corresponds to that of an LSM according to FIG. 2. However, instead of a point focus, a line is imaged in the focus and the specimen to be examined is scanned in only one direction. The line is generated in front of the scanner by inserting a cylindrical lens ZL (shown in dashes in FIG. 2). A slit diaphragm is used as confocal diaphragm instead of a pinhole diaphragm in a construction of this kind. Non-descanned detection can also be carried out with this arrangement especially when using multiphoton absorption, as is shown in FIG. 2. Further, the slit diaphragm can be omitted when using multiphoton absorption.

In the embodiment example(s) described above, each individual channel detects a spectral band of the emission spectrum with a spectral width of approximately 10 nm. However, the emission of the relevant dyes for fluorescence microscopy extends over a wavelength region of several hundred nm. Therefore, a summing of the individual channels corresponding to the fluorescence bands of the utilized dyes is carried out in the arrangement according to the invention. For this purpose, a spectral scan, as it is called, which reads out the information of the individual channels, e.g., as image information, is carried out in the first step. In this connection, the specimen is advantageously irradiated with a plurality of excitation wavelengths corresponding to the utilized dyes. Accordingly, the sum of the spectral components of the individual dyes located at the image point that has just been measured is recorded for every image point.

Subsequently, the user can put together, i.e., sum, the individual channels in any desired manner to form detection bands (emission bands). The selection of the sum areas can be carried out, for example, by presenting the signals for every image point in the individual channels in a histogram. The histogram represents the sum of all emission spectra of the dyes used in the specimen. This summing is advantageously carried out corresponding to the emission spectra of the excited dyes, wherein the respective excitation wavelengths are masked or cut out and signals of different dyes in different detection bands are summed.

Figure 7A:
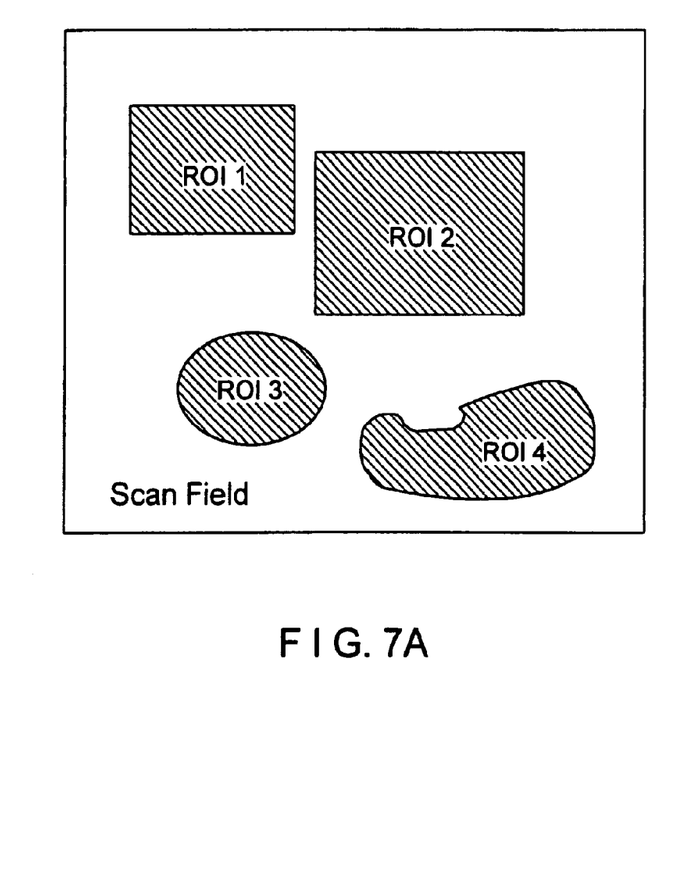
FIG. 7 is a representation of the scan field and FIG. 7b is a graphical representation of fluorescence versus wavelength.
Figure 7B:
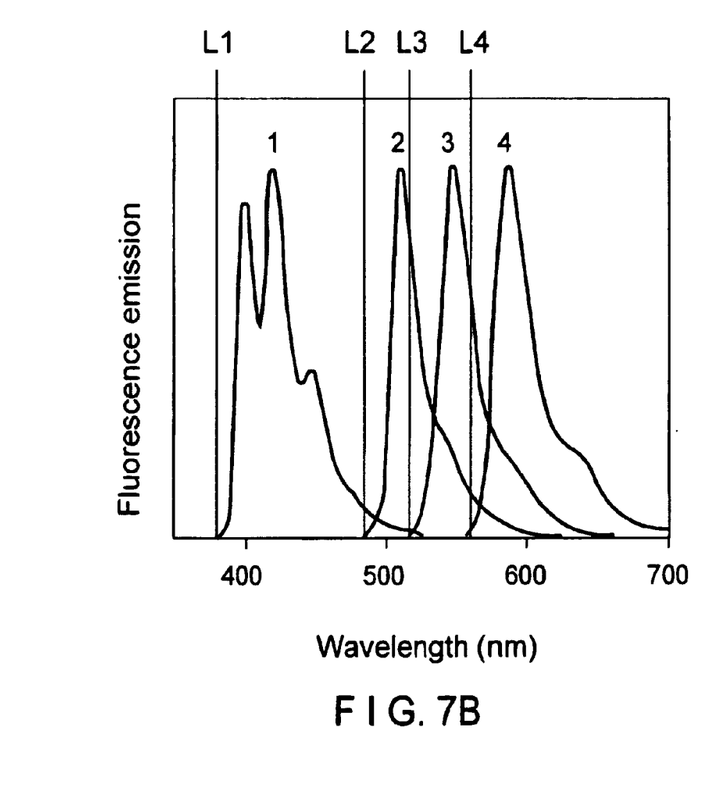

A rapid change of the detection bands for multitracking applications, i.e., for a change in the irradiation wavelength and/or the intensity during the scanning process as is described in DE 19829981A1, is possible with the arrangement according to the invention. The change can be carried out in pixel-exact manner, i.e., within a time period of several s. Therefore, it is also possible, for example, to take into account determined regions of the specimen to be examined with different detection bands (ROI tracking). FIG. 7a shows schematically a distribution of different regions of particular interest (ROI 1–4) in an LSM image representing, by way of example, different stained regions of a cell. FIG. 7b shows typical associated emission spectra 1–4 with their excitation wavelengths (L1–L4). Due to the heavy spectral overlapping of the emission spectra of the individual dyes, the use of the multitracking method CZ7302 suggests itself for detection of the individual dyes because the absorption characteristics of the individual dyes vary sharply. In this method according to the prior art, the individual dyes are selectively excited and, up to this point, four complete images are scanned one after the other in this case. A reconfiguration of the detection units according to the prior art between the individual ROIs requires the movement of mechanical detection components and is therefore impossible at a speed of several microseconds as is desirable for quick comparisons of a plurality of dynamic processes in different regions, e.g., with strongly bleaching or moving specimens and fast-running processes. However, the device according to the invention makes it possible for the user or a computer to quickly rearrange the summing bands between the individual ROIs. The specimen need only be scanned once again to record heavily overlapping ROIs. This is especially important with strongly bleaching preparations. Further, fast-running changes/contrasts between individual regions (ROIs) can be made visible. This is useful, for example, when the diffusion behavior in biological surroundings are to be examined. For this purpose, dyes are bleached at determined points in the specimen and the flowing in of new dye is subsequently examined. In another method, caged components, as the are called, are used. For example, calcium ions can be liberated in neurons by deliberate excitation of these dyes. These changes in ion concentration can subsequently be correlated with changes in other regions of the specimen.

The adjustment of the ROIs by the user can take place in the following manner, for example: After the spectral scan is taken using all or most of the excitation lines needed for exciting the dyes in the individual ROIs, sum channels can be formed between the individual excitation laser lines (L1 to L2, L2 to L3, L3 to L4 and L4 according to FIG. 7b up to the maximum emission wavelength). These sum channels correspond to parts of the fluorescence bands of the individual dyes. Further, there is a simultaneous summing of the signals of different dyes in the same sum channels because of the heavy overlapping. These sum channels are subsequently deposited with color-coding in different image channels and are displayed superimposed. Because of the different local color mixes in the image channels, the various ROIs can be localized by the user or by automatic pattern recognition and special summing adjustments can be defined, for example, according to the most frequently occurring colors for the individual ROIs.

In a second method for adjusting the different ROIs, the fluorescence centroid is measured. For this purpose, all individual channels that are irradiated by excitation laser lines are switched off in the detector. Every ROI has a characteristic fluorescence centroid because of the changed emission characteristics of the respective utilized dyes.

Accordingly, the different ROIs can be distinguished by the position of the characteristic color centroid and can be made visible separately. The sum channels for the individual ROIs are then specifically adapted to the dye characteristics.

In addition, any individual channels can also be switched off by the user. This is particularly useful for suppressing one or more excitation laser lines. The sum signals are divided by one another when determining ion concentrations according to FIG. 4 and, in this way, a measurement is obtained for the level of ion concentration. When using the method in fluorescence correlation spectroscopy, an autocorrelation of a sum channel and/or a cross-correlation between a plurality of sum channels are/is carried out.

Calculation of the emission bands can be carried out in digital or analog. Both arrangements are described more fully in the following. An arrangement for digital calculation of the sum signal is shown schematically in FIG. 8. In this case, the current at the anode of a multichannel PMT is converted to voltage and amplified through the first amplifier A (connected as current-voltage converter). The voltage is fed to an integrator I which integrates the signal over a corresponding time (e.g., pixel dwell time).

Figure 8:
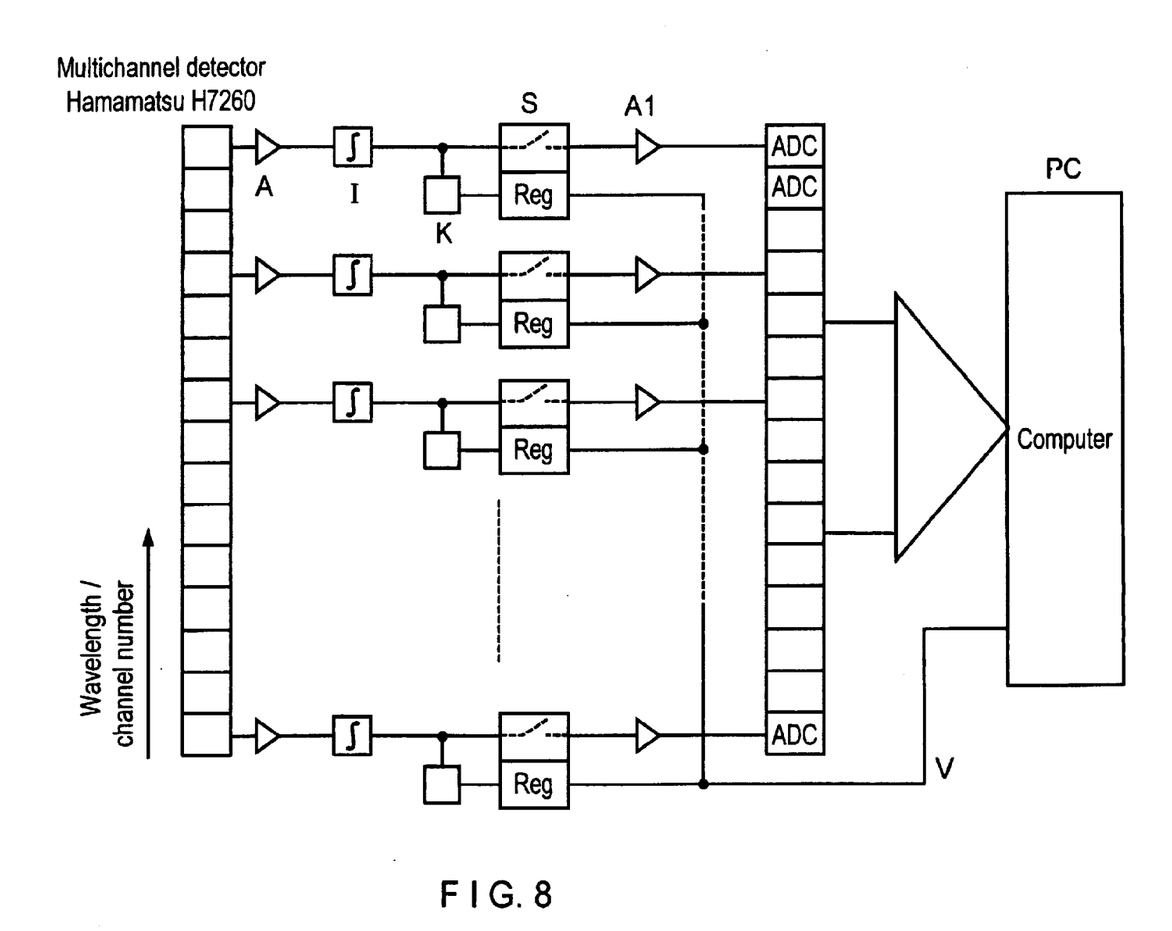
FIG. 8 is a construction example of electronics for digital evaluation.

For faster evaluation, the integrator I can be followed by a comparator K which, as a simple comparator, has a switching threshold such that a digital output signal is generated when this threshold is exceeded or which is constructed as a window comparator and then forms a digital output signal when the input signal lies between the upper and lower switching threshold or when the input signal lies outside (below or above) the switching thresholds. The comparator or window comparator can be arranged before as well as after the integrator. Circuit arrangements without an integrator (so-called amplifier mode) are also possible. With the amplifier mode arrangement, the comparator K is also present after corresponding level matching. The output of the comparator K serves as a control signal for a switch register SR which directly switches the active channels (online), or the state is conveyed to the computer via an additional connection V in order to make an individual selection of active channels (offline). The output signal of the switch register SR is fed directly to another amplifier A1 for level matching for the subsequent analog-to-digital conversion AD. The A-D-converted values are transferred via suitable data transfer to a computer (PC or digital signal processor DSP) which carries out the calculation of the sum signal(s).

Figure 9:
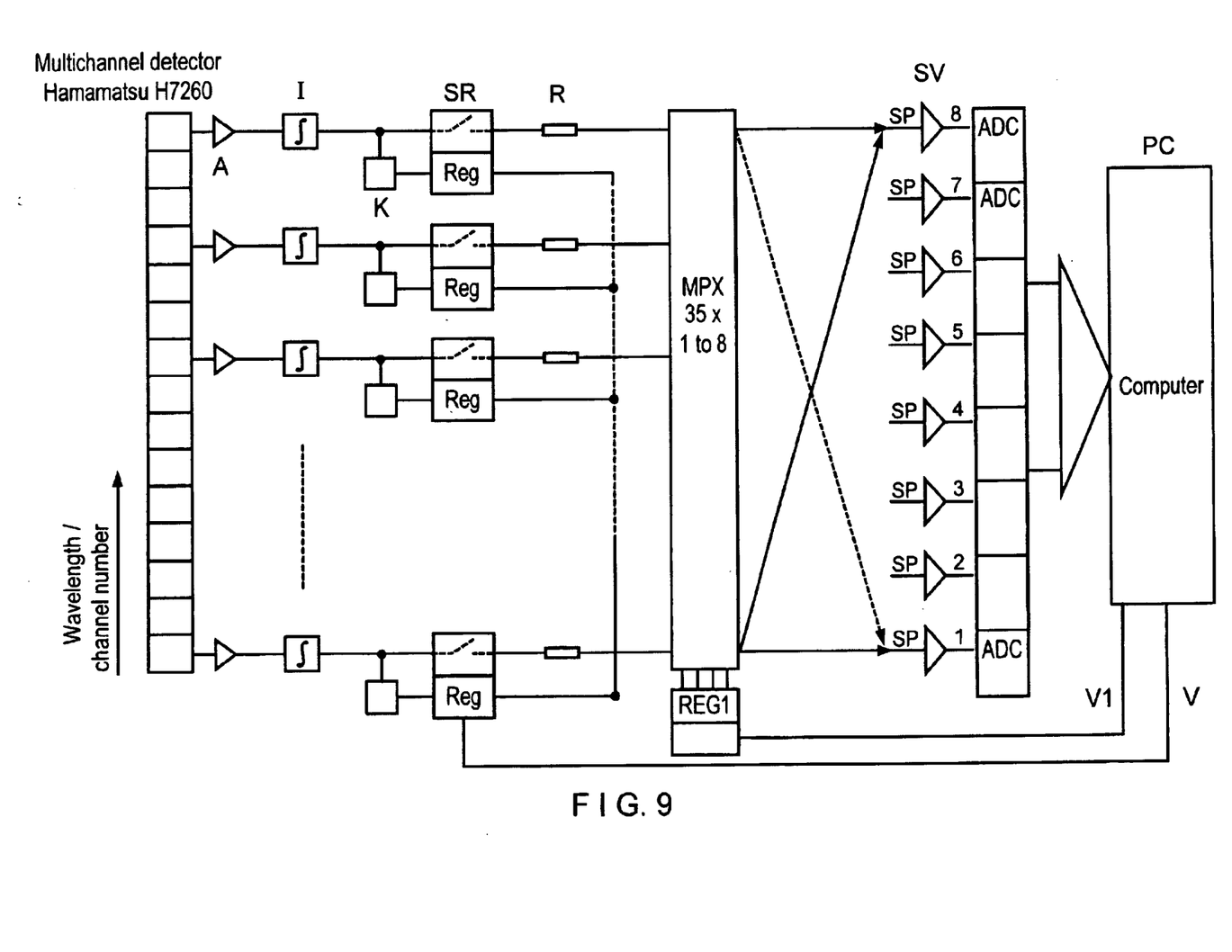
FIG. 9 is an example of construction of electronics for analog signal processing.

An equivalent of the arrangement in FIG. 8 based on analog data processing is shown in FIG. 9. The signals of the individual channels are again transformed into voltage signals by an amplifier A. Subsequently, the individual voltage signals are integrated in an integrator I during the pixel dwell time.

The integrator is followed by a comparator K which compares the integrated signal with a reference signal. If the integrated signal is smaller than the comparator threshold, then no fluorescence signal or a fluorescence signal which is too small would be measured in the corresponding individual channel. In this case, the signal of the individual channel should not be further processed because this channel only contributes a noise component to the total signal. In this case, the comparator actuates a switch S via SR and the individual channel is switched off for the pixel that has just been measured. Accordingly, by means of the comparators in combination with the switches, the relevant spectral region for the image point just measured is selected automatically.

Subsequently, the integrated voltage signal of the individual channels can be switched to different sum points by the register Reg1 with a demultiplexer MPX connected with the switch register SR. Eight different sum points are shown in FIG. 9. The register Reg1 is controlled through a control line V1 of the computer. Each sum point SP forms a portion of the summing amplifier SV carrying out the summing of the selected individual channels. A total of eight summing amplifiers SV are shown in FIG. 8. The sum signals are subsequently converted to digital signals by an analog-to-digital converter and are further processed by the computer or DSP. The sum amplifier SV can also be operated with a variable nonlinear characteristic. In another arrangement (digital (FIG. 8) and analog detection (FIG. 9)), a manipulation or distortion of the input signals of the individual detection channels is carried out: a change in the amplification of (A), a change in the integration times of (I), by inputting an additional offset before the integrator and/or by digital influence on the counted photons in a photon counting arrangement. The two methods can also be combined in any manner.

In order to prevent artifacts, it is necessary in case of fluorescence measurement to suppress the excitation light which is backscattered from the specimen or at least to attenuate it to the extent that it is less than or on the same order of magnitude as the emission maximum. To this end, the additional line filter described above or a correspondingly optimized main color splitter (MDB) can be used for optical attenuation. Since the spectral width of the exciting laser beam is very much smaller than the band width detected by the individual channel, the backscattered and reflected excitation radiation can also be carried out by deliberately switching off the corresponding individual channel with the MPX shown in FIG. 9. When the excitation wavelength occurs on two detection channels, the excitation line can be displaced by rotating the grating, displacing the line detector or tilting S1 or S2 in FIG. 6 such that it strikes only one detection channel.

The arrangement according to FIG. 9 has several advantages over the arrangement according to FIG. 8. The most striking advantage is that only the sum channels (that is, the detection bands of the utilized dyes) need to be converted to digital data and sent to the computer. This minimizes the data rates to be processed by the computer. This is particularly important when the method is applied in real-time microscopy in which, for example, more than 50 images with 512H512 pixels and a 12-bit pixel depth must be detected in order to be able to register the extremely fast-running dynamic processes. Further, when this method is used, no limits are imposed on the quantity of individual channels of the utilized line detector (matrix detector) and, accordingly, on the size of the detectable spectral region and/or the spectral resolution of the spectral sensor.

Further, in the device shown in FIG. 8, the signal level to be converted is substantially smaller. The expected signal-to-noise ratio is therefore lower.

In the two arrangements described above, an integrator circuit was advantageously used to detect the individual channel signals. However, photon counting can also be carried out in the individual channels without restrictions and the photon counts are added. But the arrangement shown in FIG. 8 has the advantage that it also provides, in addition to the sum signals, complete spectral information for subsequent image processing. Therefore, the invention also includes a combination of the two arrangements.

While the foregoing description and drawings represent the present invention, it will be obvious to those skilled in the art that various changes may be made therein without departing from the true spirit and scope of the present invention.

What is claimed is:

1. A method for operation of an image-generating optical system for detection of characteristic quantities of the wavelength-dependent behavior of an illuminated specimen, such as the emission behavior and/or absorption behavior and, in particular, the fluorescence and/or luminescence and/or phosphorescence and/or enzyme-active light emission and/or enzyme-active fluorescence, for the operation of a laser scanning microscope, comprising the steps of:

splitting the image point information of the specimen into spectral components in a spatially resolved manner on the detection side in dependence on wavelength; and carrying out at least one summing for different spectral components, wherein a change in at least one irradiation wavelength and/or irradiation intensity is carried out within a scanning process between different specimen regions and a summing of at least some of the respective spectral components is carried out for different specimen regions and/or irradiation wavelengths/intensities;

displaying the summed regions as images.

2. The method according to claim 1, wherein a plurality of partial sums is formed and then added.

3. The method according to claim 1, with an overlapping of partial sums of spectral components containing the overlapped signals of different fluorescence components.

4. The method according to claim 1, further including determining spectral centroid formation for a plurality of spectral components.

5. The method according to claim 1, with mathematical combination such as division and subtraction of partial sums or individual components and graphic representation of the combination.

6. The method according to claim 1, for optical detection of characteristic quantities of the wavelength-dependent behavior of an illuminated specimen, such as the emission behavior and/or absorption behavior, in particular, the fluorescence and/or luminescence and/or phosphorescence and/or enzyme-active light emission and/or enzyme-active fluorescence, wherein the emission radiation is split spectrally by a dispersive element, detected in a spatially resolved manner and at least one sum signal of the emission radiation and/or of the absorbed radiation is determined electronically.

7. The method according to claim 1, wherein the sum signal of the spectrally split emission radiation is determined for distinguishing different dyes and/or for determining the local dye composition of an image point when a plurality of dyes are used simultaneously and/or for determining the local shift of the emission spectrum depending on the local environment to which the dye or dyes is or are attached and/or for measuring emission ratio dyes for determining ion concentrations.

8. The method according to claim 1, wherein the sum signal of the spectrally expanded, reflected, backscattered and/or transmitted excitation radiation of fluorochromes is carried out for distinguishing different dyes and/or for determining the local dye composition of an image point when a plurality of dyes are used simultaneously and/or for determining the local shift in the absorption spectrum depending on the local environment to which the dye or dyes is or are attached and/or for measuring the absorption ratio for determining ion concentrations.

9. The method according to claim 1, wherein the composition of the sum signals can be varied during scanning as a function of the excitation parameters (multitracking).

10. The method according to claim 1, wherein the composition of the sum signals can be varied during scanning as a function of the respective scanning position (ROI tracking).

11. The method according to claim 1, wherein the emission radiation of the specimen is split by a dispersive element and is detected in a spatially resolved manner in at least one direction.

12. The method according to claim 1, wherein a splitting of the fluorescence radiation is carried out.

13. The method according to claim 1, wherein the radiation that is reflected, backscattered and/or transmitted by the specimen is split by a dispersive element and is detected in a spatially resolved manner in at least one direction for absorption measurement.

14. The method according to claim 1, wherein the signals of detection channels are converted and digitally read out and summing is carried out digitally in a computer.

15. The method according to claim 1, wherein the summing is carried out with analog data processing by a demultiplexer in combination with a summing amplifier.

16. The method according to claim 1, wherein the signals of detector channels are influenced by a nonlinear distortion of the input signals.

17. The method according to claim 1, further comprising integrating the signal from a detection channel over a predetermined time.

18. The method according to claim 1, wherein the characteristic or response curve of an amplifier is influenced.

19. The method according to claim 1, wherein the sum signal is used for generating an image.

20. The method according to claim 1, wherein a color-coded fluorescence image is generated.

21. The method according to claim 1, wherein a superposition is carried out with additional images.

22. The method according to claim 1, wherein the sum signals are combined with a lookup table.

23. The method according to claim 1, wherein representation of different dyes and/or the spread of the generated image is carried out by the lookup table.

24. The method according to claim 1, wherein a comparison of the measured signal with a reference signal is carried out via comparators in detection channels and in case the reference signal is not reached and/or is exceeded a change in the operating mode of the detection channel is carried out.

25. The method according to claim 1, wherein the respective detection channel is switched off and/or not taken into account.

26. The method according to claim 25, wherein the spectral region of interest is narrowed in this way.

27. The method according to claim 1, wherein the signals of the detection channels are generated by at least one integrator circuit.

28. The method according to claim 1, wherein the signals of the detection channels are generated by photon counting and subsequent digital-to-analog conversion.

29. The method according to claim 28, wherein photon counting is carried out in time correlation.

30. The method according to claim 1, for detection of single-photon and/or multiphoton fluorescence and/or fluorescence excited by entangled photons.

31. The method according to claim 1, with parallel illumination and detection, such as in ingredient screening, wherein the specimen is a microtiter plate.

32. The method according to claim 1, incorporated in a microscope.

33. The method according to claim 1, for detection in a nearfield scanning microscope.

34. The method according to claim 1, for detection of a single-photon and/or multiphoton dye fluorescence in a fluorescence-correlated spectroscope.

35. The method according to claim 1, employing confocal detection.

36. The method according to claim 1, employing a scanning arrangement.

37. The method according to claim 1, employing illumination means with an X-Y scanner.

38. The method according to claim 1, employing an X-Y scan table.

39. The method according to claim 1, employing nonconfocal detection.

40. The method according to claim 1, employing a scanning arrangement.

41. The method according to claim 1, employing descanned detection.

42. The method according to claim 1, employing brightfield imaging.

43. The method according to claim 1, employing point imaging.

44. The method according to claim 1, employing nondescanned detection.

45. The method according to claim 1, employing nonscanning, confocal or nonconfocal detection and point imaging or brightfield imaging.

46. An arrangement for optical detection of characteristic quantities of the wavelength-dependent behavior of an illuminated specimen, such as the emission behavior and/or absorption behavior and, in particular, the fluorescence and/or luminescence and/or phosphorescence and/or enzyme-active light emission and/or enzyme-active fluorescence, comprising:

a dispersive element for splitting the emission radiation spectrally;

a detector for detecting a radiation signal; and means for electronically determining at least one sum signal of the emission radiation and/or of the absorbed radiations;

wherein a change in at least one irradiation wavelength and/or irradiation intensity is carried out within a scanning process between different specimen regions and a summing of at least some of the respective spectral components is carried out for different specimen regions and/or irradiation wavelengths/intensities.

47. The arrangement according to claim 46, wherein the sum signal of the spectrally split emission radiation is determined for distinguishing different dyes and/or for determining the local dye composition of an image point when a plurality of dyes are used simultaneously and/or for determining the local shift of the emission spectrum depending on the local environment to which the dye or dyes is or are attached and/or for measuring emission ratio dyes for determining ion concentrations.

48. The arrangement according to claim 46, wherein the sum signal of the spectrally expanded, reflected, backscattered and/or transmitted excitation radiation of fluorochromes is carried out for distinguishing different dyes and/or for determining the local dye composition of an image point when a plurality of dyes are used simultaneously and/or for determining the local shift in the absorption spectrum depending on the local environment to which the dye or dyes is or are attached and/or for measuring the absorption ratio for determining ion concentrations.

49. The arrangement according to claim 46, wherein the composition of the sum signals can be varied during scanning (multitracking).

50. The arrangement according to claim 46, wherein the composition of the sum signals can be varied during scanning (ROI tracking).

51. The arrangement according to claim 46, wherein the emission radiation of the specimen is split by a dispersive element and is detected in a spatially resolved manner in at least one direction.

52. The arrangement according to claim 46, wherein a splitting of the fluorescence radiation is carried out.

53. The arrangement according to claim 46, wherein the radiation that is reflected or transmitted by the specimen is split by a dispersive element and is detected in a spatially resolved manner in at least one direction for absorption measurement.

54. The arrangement according to claim 46, wherein the signals of detection channels are converted and digitally read out and summing is carried out digitally in a computer.

55. The arrangement according to claim 46, wherein the summing is carried out with analog data processing by a demultiplexer in combination with a summing amplifier.

56. The arrangement according to claim 46, wherein the signals of detector channels are influenced by a nonlinear distortion of the input signals.

57. The arrangement according to claim 46, further comprising integrating the signal from a detection channel over a predetermined time.

58. The arrangement according to claim 46, wherein the characteristic or response curve of an amplifier is influenced.

59. The arrangement according to claim 46, wherein the sum signal is used for generating an image.

60. The arrangement according to claim 46, wherein a color-coded fluorescence image is generated.

61. The arrangement according to claim 46, wherein a superposition is carried out with additional images.

62. The arrangement according to claim 46, wherein the sum signals are combined with a lookup table.

63. The arrangement according to claim 46, wherein representation of different dyes and/or the spread of the generated image is carried out by the lookup table.

64. The arrangement according to claim 46, wherein a comparison of the measured signal with a reference signal is carried out via comparators in detection channels and in case the reference signal is not reached and/or is exceeded a change in the operating mode of the detection channel is carried out.

65. The arrangement according to claim 46, wherein the respective detection channel is switched off and/or not taken into account.

66. The arrangement according to claim 65, wherein the spectral region of interest is narrowed in this way.

67. The arrangement according to claim 46, wherein the signals of the detection channels are generated by at least one integrator circuit.

68. The arrangement according to claim 46, wherein the signals of the detection channels are generated by photon counting and subsequent digital-to-analog conversion.

69. The arrangement according to claim 68, wherein photon counting is carried out in time-correlated manner.

70. The arrangement according to claim 46, for detection of single-photon and/or multiphoton fluorescence and/or fluorescence excited by entangled photons.

71. The arrangement according to claim 46, with parallel illumination and detection, such as in ingredient screening, wherein the specimen is a microtiter plate.

72. The arrangement according to claim 46, incorporated in a microscope.

73. The arrangement according to claim 46, for detection in a nearfield scanning microscope.

74. The arrangement according to claim 46, for detection of a single-photon and/or multiphoton dye fluorescence in a fluorescence-correlated spectroscope.

75. The arrangement according to claim 46, employing confocal detection.

76. The arrangement according to claim 46, employing a scanning arrangement.

77. The arrangement according to claim 46, employing an X-Y scanner in the illumination means.

78. The arrangement according to claim 46, employing an X-Y scan table.

79. The arrangement according to claim 46, employing nonconfocal detection.

80. The arrangement according to claim 46, employing a scanning arrangement.

81. The arrangement according to claim 46, employing descanned detection.

82. The arrangement according to claim 46, employing brightfield imaging.

83. The arrangement according to claim 46, employing point imaging.

84. The arrangement according to claim 46, employing non-descanned detection.

85. The arrangement according to claim 46, employing non-scanning, confocal or nonconfocal detection and point imaging or brightfield imaging.

86. A method for operation of an image-generating optical system for detection of characteristic quantities of the wavelength-dependent behavior of an illuminated specimen, such as the emission behavior and/or absorption behavior and, in particular, the fluorescence and/or luminescence and/or phosphorescence and/or enzyme-active light emission and/or enzyme-active fluorescence, for the operation of a laser scanning microscope, comprising the steps of:

splitting the image point information of the specimen into spectral components in a spatially resolved manner on the detection side in dependence on wavelength; and carrying out at least one summing for different spectral components, wherein a change in at least one irradiation wavelength and/or irradiation intensity is carried out within a scanning process between different specimen regions and a summing of at least some of the respective spectral components is carried out for different specimen regions and/or irradiation wavelengths/intensities;

wherein the composition of the sum signals can be varied during scanning as a function of the excitation parameters (multitracking) or as a function of the respective scanning position (ROI tracking);

displaying the summed regions as images.

* * * * *